United States Patent [19]

Rauscher et al.

[11] 4,066,508
[45] Jan. 3, 1978

[54] PROCESS AND REAGENT FOR DETERMINING TRIGLYCERIDES

[75] Inventors: Elli Rauscher; Erich Bernt, both of Munich; Wolfgang Gruber, Tutzing-Unterzeismering; Helmut Determann, Starnberg, all of Germany

[73] Assignee: Boehringer Mannheim GmbH, Mannheim-Waldhof, Germany

[21] Appl. No.: 707,455

[22] Filed: July 21, 1976

[30] Foreign Application Priority Data

Aug. 12, 1975 Germany .............................. 2535953

[51] Int. Cl.$^2$ ............................................... C12K 1/00
[52] U.S. Cl. ............................... 195/99; 195/103.5 R
[58] Field of Search ................. 195/103.5 R, 99, 100; 23/230 B

[56] References Cited

U.S. PATENT DOCUMENTS

| 3,853,465 | 12/1974 | Rush et al. .......................... 23/230 B |
| 3,862,009 | 1/1975 | Wahlefeld et al. ............ 195/103.5 R |
| 4,011,045 | 3/1977 | Bonderman ......................... 23/230 B |
| 4,012,287 | 3/1977 | Carl ............................... 195/103.5 R |

*Primary Examiner*—Lionel M. Shapiro
*Attorney, Agent, or Firm*—Burgess, Dinklage & Sprung

[57] ABSTRACT

Triglycerides are determined by enzymatic saponification with lipase in a buffer in the presence of a carboxylesterase and an alkali metal or alkaline earth metal (10–15 carbon atom) alkyl sulfate, in the additional presence of a compound of the general formula $RO(CH_2CH_2)_nH$, in which R is alkyl or alkenyl containing 14 to 20 carbon atoms and $n$ is a number of from 7 to 20; this determination prevents turbidity and does not disadvantageously influence enzyme activity.

16 Claims, No Drawings

PROCESS AND REAGENT FOR DETERMINING TRIGLYCERIDES

The present invention is concerned with a process and reagent for the determination of triglycerides.

It is known to determine triglycerides by enzymatic saponification with lipase, which is preferably obtained from *Rhizopus arrhizus*, and measurement of the liberated glycerol, wherein the saponification is carried out in a buffer in the presence of carboxylesterase and an alkali metal or alkaline earth metal alkyl sulfate, the alkyl radical of which contains 10 to 15 carbon atoms (see British Pat. No. 1,395,126).

A disadvantage of this process is that, in some cases and especially in the case of strongly lipaemic sera, turbidities arise due to the liberation of fatty acids which considerably disturb optical determination. In principle, it is possible to keep fatty acids in solution by the addiiton of surface-active agents but the amounts of surface-active agents necessary for this inhibit the enzymes. The investigation of a very large number of substances with a surface-active action showed that none of them was able satisfactorily to fulfill both requirements i.e., prevention of turbidity and no disturbances of the enzyme activities.

The present invention provides a process and a reagent for the determination of triglycerides which enables a completely enzymatic saponification and determination, prevents the turbidity due to liberated fatty acids and does not disadvantageously influence the enzyme activities.

The present invention, provides a process for the determination of triglycerides by enzymatic saponification with lipase in a buffer in the presence of a carboxylesterase and of an alkali metal or alkaline earth metal alkyl sulfate, the alkyl radical of which contains 10 to 15 carbon atoms, wherein a compound of the general formula $RO(CH_2CH_2O)_nH$, in which R is an alkyl or alkenyl radical containing 14 to 20 carbon atoms and $n$ is a number of from 7 to 20, is also added.

German Pat. No. 2,327,894 describes a process for the prevention of the turbidity of blood samples or serum which is due to triglycerides but not due to the saponification products thereof. According to this process, a polyoxyethylated lauric acid compound containing 9 to 10 mole ethylene oxide is added to the sample. Experiments showed that, with this agent, the turbidity arising in the case of enzymatic splitting of the triglycerides cannot be prevented and, furthermore, an inhibition of the lipolysis occurs. Therefore, the above-mentioned compound is unsuitable for the solving of the problem forming the basis of the present invention.

For the process according to the present invention, it is preferable to use a lipase from *Rhizopus arrhizus*. However, other lipases can also be employed without the reaction time and reaction temperature having to be increased. The usability of a lipase within the scope of the process of the present invention is partially also determined by the carboxylesterase, a known esterase from micro-organisms preferably being employed as carboxylesterase. The activation of the lipase by the alkyl sulfate taking place according to British Pat. No. 1,395,126 is thereby not only maintained but it is even possible still further to reduce the reaction time and temperature in comparison with the process of the British Patent.

According to the present invention, compounds are preferred of the above-given general formula in which $n$ is a number of from 9 to 15, those in which $n$ is 12 being especially preferred.

The compounds of the above-given general formula are preferably used in amounts of 0.005 to 0.2 wt.% referred to the volume of the buffer solution, amounts of 0.01 to 0.03 wt.% being especially preferred.

The process conditions and other additives are substantially the same as in the above-mentioned British Pat. No. 1,395,126. An addition of serum albumin, especially of bovine serum albumin, is preferred when the sample contains triglycerides not associated to protein.

In contradistinction to our above-mentioned British Patent, in the case of the process of the present invention, phosphate buffer can also be used and is even preferred, 0.02 to 0.1M and preferably 0.05M phosphate buffer of pH 6.5 to 8.0 having proved to be especially useful.

The reagent according to the present invention for the carrying out of the process of the present invention comprises lipase, especially from *Rhizopus arrhizus*, carboxylesterase, an alkali metal or alkaline earth metal alkyl sulfate, the alkyl radical of which contains 10 to 15 carbon atoms, a buffer and a system for the detection of glycerol, as well as a compound of the general formula $RO(CH_2CH_2O)_nH$, wherein R is an alkyl or alkenyl radical containing 14 to 20 carbon atoms and $n$ is a number of from 7 to 20.

As in the case of our above-mentioned British Patent, any system can, in principle, be employed for the detection of glycerol but it is preferred to use a detection system comprising NADH, ATP, PEP, LDH, PK and GK, as well as magnesium ions and a buffer.

An especially preferred reagent according to the present invention comprises:

0.1 to 10.0 mg./ml. lipase from *Rhizopus arrhizus*,
0.01 to 20.0 mg./ml. carboxylesterase from micro-organisms,
0.01 to 0.2 mg./ml. sodium dodecyl sulfate,
0.015 to 0.3 mg./ml cetyl stearyl polyglycol ether containing 12 mole ethylene oxide,
1 to 20 mM nicotinamide-adenine-dinucleotide in reduced form (NADH),
10 to 100 mM adenosine triphosphate (ATP),
2 to 20 mM phosphoenol pyruvate (PEP),
0.5 to 5 mg./ml. lactate dehydrogenase (LDH),
0.2 to 5 mg./ml. phosphoenol kinase (PK),
0.05 to 10 mg./ml. glycerokinase (GK),
0.1 to 2.0 mg./ml. serum albumin,
3 to 30 mM magnesium ions, and
0.012 to 0.3M buffer solution of pH 6 to 9.

The process according to the present invention further increases the precision of the determination. Furthermore, it is possible to reduce the time needed for the process to 10 minutes and also to work at ambient temperature.

The following Examples are given for the purpose of illustrating the present invention.

EXAMPLE 1

A reagent according to the present invention was prepared from
1. Buffer Solution
   0.05M sodium phosphate buffer pH 7.0 containing
   4 mM magnesium sulfate 0.01% sodium dodecyl sulfate
0.015% cetyl stearly alcohol polyglycol ether containing 12 mole ethylene oxide
2. Coenzyme Mixture
10 mM NADH
22 mM ATP sodium salt
18 mM PEP-CHA salt
3. Enzyme Mixture
400 U/ml. lipase (*Rhizopus arrhizus*)
50 U/ml. carboxylesterase (from microorganisms)
50 U/ml. PK (rabbit muscle)
300 U/ml. LDH (pig heart) as a suspension in aqueous ammonium sulfate solution
4. 150 U/ml. glycerokinase, suspended in aqueous ammonium sulfate solution.

Mixtures 1 to 4 are stable for at least 1 year at $+4°$ C. After dissolving at this temperature, mixture 2 is stable for about 2 weeks.

A reaction mixture was prepared from reagents 1 to 3 which, when cooled, was stable for about 2 days. For this purpose, mixture 2 previously was dissolved in distilled water. For the finished reaction mixture, solutions 1 and 2 and suspension 3 were then mixed in the volume ratio of 50:1. 0:1.0.

The determination can be carried out with or without a sample blank.

Carrying out the determination with sample blank:

5.0 ml. reaction mixture of 1, 2, 3 were mixed with 0.1 ml. serum. 2.0 to 2.5 ml. thereof were taken and mixed with 0.01 ml. suspension 4 (sample); the remainder serves as sample blank. Both solutions were left to stand for about 10 minutes at $20°$ to $25°$ C. and the extinction of the sample is measured against the sample blank. The found value was used for the calculation.

Determination without sample blank:

2.5 ml. of the reaction mixture of 1, 2 and 3 were mixed with 0.05 ml. serum, left to stand for about 10 minutes at $20°$ to $25°$ C. and then the extinction of this solution read off. 0.01 ml. suspension 4 were then admixed and, after 10 minutes, the extinction was again read off. The difference of both measurements was used for the calculation. The measurement takes place in a photometer at 365 nm, 340 nm or 334 nm.

The calculation takes place, depending upon the measurement wavelength, by multiplication of the extinction difference by 15.5 (365 nm) or 8.23 (340 nm) or 8.53 (334 nm), the result thereby being obtained in mMol triglyceride per liter of sample.

Repetition of the determination with differing amounts of triglyceride in the serum gave a line, the proportionality $r$ (correlation coefficient) being 0.997.

EXAMPLE 2

For the comparison of the process or reagent according to the present invention with the process or reagent of British Pat. No. 1,395,126, the following experiments were carried out:

Experiments 1 and 2

4.9 ml. compound 1 of Example 1 of British Pat. No. 1,395,126.
0.2 ml. component 2 of Example 1 of British Pat. No. 1,395,126
0.1 ml. component 3 + 4 of Example 1 of British Pat. No. 1,395,126
0.1 ml. serum (approximately 500 mg.% triglycerides) were mixed. 2.5 ml. of this solution were placed in cuvette 1 and the remainder in cuvette 2.

Experiment 3 and 4

5 ml. compound 1 according to Example 1 hereof
0.1 ml. component 2 according to Example 1 hereof
0.1 ml. component 3 according to Example 1 hereof
0.1 ml. serum (as in the case of experiment 1 and 2) were mixed.

2.5 ml. of the solution obtained were placed in cuvette 3 and the remainder in cuvette 4.

After about 20 minutes, 0.01 ml. GK suspension were pipetted into each of cuvettes 1 and 3. Cuvettes 2 and 4 served as sample blanks.

Results

1. Finding According to Evaluation with Sample Blank cuvette 1/2 517 mg. triglyceride/100 ml. serum  } after
cuvette 3/4 508 mg. triglyceride/100 ml. serum  } 10 min.

Finding according to evaluation without sample blank:
cuvette 1 477 mg. triglyceride/100 ml. serum  } after
cuvette 3 513 mg. triglyceride/100 ml. serum  } 10 min.

With the reagent according to the present invention, practically identical values were obtained without and with regard to the sample blank. With the reagent of British Pat. No. 1,395,126, deviating results were obtained (caused by the appearance of turbidity); in the present example, the differences were about 8%. p 2. Turbidity Immediately after the addition of the sample, all the experimental batches were almost clear. In cuvette 1 and 2, a noticeable turbidity occurs after 5 minutes. In cuvettes 3 and 4, clearing occurs after 0.5 minutes. After 55 minutes, the solution in cuvette 4 was still clear, whereas in cuvette 2 it was very cloudy.

It will be understood that the specification and examples are illustrative but not limitative of the present invention and that other embodiments within the spirit and scope of the invention will suggest themselves to those skilled in the art.

What is claimed is:

1. Process for the determination of triglycerides comprising enzymatically saponifying the triglycerides with lipase in the buffer in the presence of a carboxylesterase and of an alkali metal of alkaline earth metal alkyl sulfate, the alkyl radical of which contains 10 to 15 carbon atoms, in the additional presence of a compound of the formula $RO(CH_2CH_2O)_nH$, in which R is alkyl or alkenyl of from 14 to 20 carbon atoms and $n$ is an integer of from 7 to 20.

2. Process as claimed in claim 1 wherein $n$ is an integer from 9 to 15.

3. Process as claimed in claim 1 wherein $n$ is 12.

4. Process as claimed in claim 1 wherein the compound of the formula $RO(CH_2CH_2O)_nH$ is added in an amount of from 0.005 to 0.2 wt. percent per volume of buffer.

5. Process as claimed in claim 1 wherein the compound of the formula $RO(CH_2CH_2O)_nH$ is added in an amount of from 0.01 to 0.03 wt. percent per volume of buffer.

6. Process as claimed in claim 1 wherein there is additionally present serum albumin.

7. Process as claimed in claim 1 wherein said lipase is obtained from *Rhizopus arrhizus*.

8. Process as claimed in claim 1 wherein said buffer is a phosphate buffer.

9. Process as claimed in claim 8 wherein a 0.02 to 0.1M phosphate buffer of pH 6.5 to 8.0 is used.

10. Reagent for the determination of triglycerides, comprising lipase, carboxylesterase, an alkali metal or alkaline earth metal alkyl sulfate of from 10 to 15 carbon atoms in the alkyl radical, a buffer, a system for the detection of glycerol, and a compound of the general formula $RO(CH_2CH_2O)_nH$ wherein R is alkyl or alkenyl of from 14 to 20 carbon atoms and $n$ is an integer of from 7 to 20.

11. Reagent as claimed in claim 10 wherein the system for the detection of glycerol comprises nicotinamide-adenine-dinucleotide in reduced form, adenosine triphosphate, phosphoenol pyruvate, lactate dehydrogenase, pyruvate kinase, glycerokinase, magnesium ions and a buffer.

12. Reagent as claimed in claim 10 additionally comprising serum albumin.

13. Reagent according to claim 10 wherein the lipase used is lipase from *Rhizopus arrhizus*.

14. Reagent as claimed in claim 10 comprising:

0.1 to 10.0 mg./ml. lipase from *Rhizopus arrihizus*,
0.01 to 20.0 mg./ml. carobxylesteresterase from microorganisms,
0.01 to 0.2 mg./ml. sodium dodecyl sulfate,
0.015 to 0.3 mg./ml. cetyl stearyl polyglycol ether containing 12 mole ethylene oxide,
1 to b 20 mM nicotinamide-adenine-dinucleotide in reduced form,
10 to 100 mM adenosine triphosphate
2 to 20 mM phosphoenol pyruvate,
0.5 to 5 mg./ml. lactate dehydrogenase,
0.2 to 5 l mg./ml. phosphoenol kinase,
0.05 to 10 mg. glycerokinase,
0.1 to 2.0 mg./ml. serum albumin,
3 to 30 mM magnesium ions and
0.012 to 0.3 M buffer solution of pH 6 to 9.

15. Reagent according to claim 11 wherein the buffer used is a 0.02 – 0.1 M phosphate buffer of pH 6.5 to 8.0.

16. Reagent according to claim 15 wherein the buffer is a 0.05 M sodium phosphate buffer.

* * * * *